United States Patent

Stach

[11] 4,163,112
[45] Jul. 31, 1979

[54] O-ALKOXY- AND ALKYLTHIOPHENYL CARBAMATES

[75] Inventor: Leonard J. Stach, Riverside, Ill.

[73] Assignee: Velsicol Chemical Corporation, Chicago, Ill.

[21] Appl. No.: 784,213

[22] Filed: Apr. 4, 1977

[51] Int. Cl.² ............... C07C 125/06; A61K 31/27
[52] U.S. Cl. .................................... 560/132; 560/9; 560/22; 560/29; 560/31; 560/115; 560/135; 560/137; 424/300
[58] Field of Search ............... 260/471 C, 479 C; 560/132, 135, 137

[56] References Cited

U.S. PATENT DOCUMENTS

| | | | |
|---|---|---|---|
| 3,780,104 | 12/1973 | Teach | 260/471 C |
| 3,781,301 | 12/1973 | Nikles et al. | 260/479 C |
| 3,843,720 | 10/1974 | Nikles | 260/479 C |
| 3,910,991 | 10/1975 | Nikles | 260/479 C |
| 3,962,316 | 6/1976 | Kiehs et al. | 260/479 C |

FOREIGN PATENT DOCUMENTS 2252198  5/1974  Fed. Rep. of Germany ....... 260/479 C Primary Examiner—James O. Thomas, Jr.
Assistant Examiner—G. T. Breitenstein
Attorney, Agent, or Firm—Robert J. Schwarz; Dietmar Olesch

[57] ABSTRACT

This invention discloses new chemical compounds of the formula

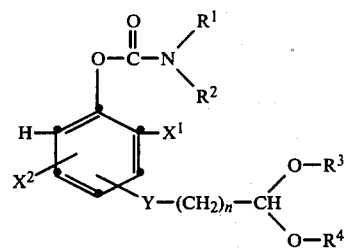

wherein $R^1$ is selected from the group consisting of hydrogen, alkyl and alkenyl; $R^2$ is selected from the group consisting of alkyl, alkenyl, cycloalkyl and

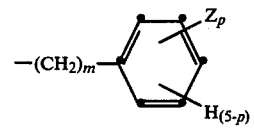

wherein Z is selected from the group consisting of alkyl, alkenyl, alkoxy, halogen, nitro and alkylthio; p is an integer from 0 to 5; and m is the integer 0 or 1; $X^1$ and $X^2$ are each selected from the group consisting of hydrogen, alkyl and halogen; Y is selected from the group consisting of oxygen and sulfur; n is the integer 1 or 2; and $R^3$ and $R^4$ are each alkyl.

5 Claims, No Drawings

O-ALKOXY- AND ALKYLTHIOPHENYL CARBAMATES

This invention relates to new compositions of matter and more specifically relates to new chemical compounds of the formula

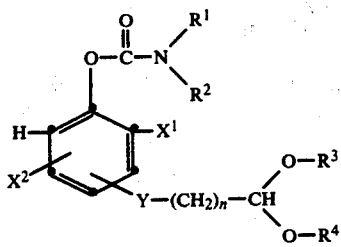

wherein $R^1$ is selected from the group consisting of hydrogen, alkyl and alkenyl; $R^2$ is selected from the group consisting of alkyl, alkenyl, cycloalkyl and

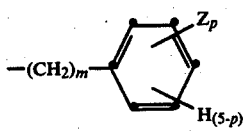

wherein Z is selected from the group consisting of alkyl, alkenyl, alkoxy, halogen, nitro and alkylthio; p is an integer from 0 to 5; and m is the integer 0 or 1; $X^1$ and $X^2$ are each selected from the group consisting of hydrogen, alkyl and halogen; Y is selected from the group consisting of oxygen and sulfur; n is the integer 1 or 2; and $R^3$ and $R^4$ are each alkyl.

In a preferred embodiment of the present invention $R^1$ is selected from the group consisting of hydrogen, lower alkyl and lower alkenyl; $R^2$ is selected from the group consisting of lower alkyl, lower alkenyl, cycloalkyl of from 3 to 7 carbon atoms and

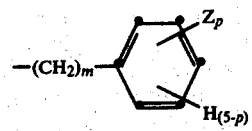

wherein Z is selected from the group consisting of lower alkyl, lower alkenyl, lower alkoxy, chlorine, bromine, fluorine, nitro and lower alkylthio; p is an integer of from 0 to 3; and m is the integer 0 or 1; $X^1$ and $X^2$ are each selected from the group consisting of hydrogen, lower alkyl, chlorine and bromine; Y is selected from the group consisting of oxygen and sulfur; n is the integer 1 to 2; and $R^3$ and $R^4$ are each lower alkyl.

The term "lower" as used herein designates a straight or branched carbon chain of up to six carbon atoms.

The compounds of the present invention are useful as insecticides.

The compounds of the present invention can be prepared by reacting a compound of the formula

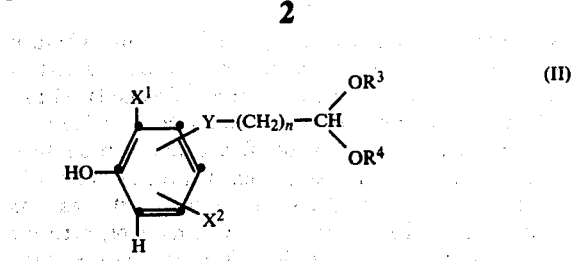

wherein $X^1$, $X^2$, Y, n, $R^3$ and $R^4$ are as heretofore described with a carbamoyl chloride of the formula

wherein $R^1$ and $R^2$ are as heretofore described. This reaction can be effected by incrementally adding the carbamoyl chloride of formula III to a solution of the compound of formula II in an inert organic reaction medium at room temperature and in the presence of an acid acceptor such as an alkali metal carbonate or bicarbonate or a tertiary amine. About equimolar amounts of the reactants can be effectively used. After the addition is completed, the reaction mixture can be heated at its reflux temperature for a period of up to about several hours to ensure completion of the reaction.

The compounds of the present invention wherein $R^1$ is hydrogen can also be prepared by reacting the compound of formula II with an isocyanate of the formula

wherein $R^2$ is as heretofore described. This reaction can be effected by incrementally adding an equimolar or slight excess molar amount of the isocyanate to a solution of the compound of formula II in an inert organic solvent such as benzene at room temperature. A catalytic amount of triethylamine can be used to aid in the reaction. After the isocyanate addition is completed, the reaction mixture can be stirred for an additional period of up to about 8 hours to ensure completion of the reaction. After this time the reaction mixture can be filtered and the filtrate stripped of solvent to yield the desired product, which can be used as such or can be further purified by standard techniques well known in the art.

The compounds of formula II can be prepared by reacting a compound of the formula

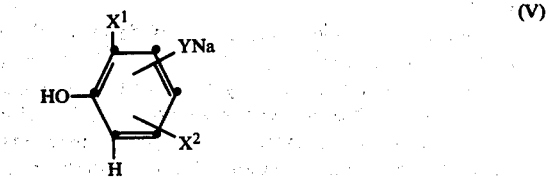

wherein $X^1$, $X^2$ and Y are as heretofore described, with a compound of the formula

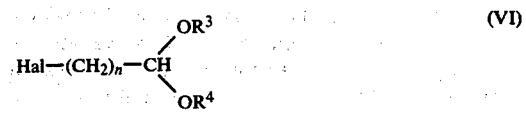

wherein Hal designated halogen and n, $R^3$ and $R^4$ are as heretofore described. This reaction can be effected by incrementally adding the compound of formula VI to a solution of the compound of formula V in an inert organic solvent such as dimethylformamide at room temperature. About equimolar amounts of the reactants can be utilized. After the addition is completed, the reaction mixture can be heated under a nitrogen atmosphere at a temperature ranging up to the reflux temperature of the mixture for a period of up to about 50 hours. After this time water can be added to the reaction mixture and the mixture neutralized. The organic phase can then be separated from the aqueous phase and can be stripped of solvent to yield the desired product. This product can be used as such or can be further purified as desired.

The compounds of formula V can be prepared by reacting a compound of the formula

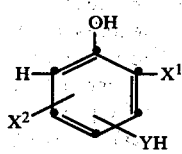

(VII)

wherein $X^1$, $X^2$ and Y are as heretofore described, with an equimolar amount of sodium methoxide. This reaction can be effected by combining an alcoholic solution of sodium methoxide with a solution of the compound of formula VII in methanol at room temperature with stirring. After the addition is completed, the mixture can be warmed and stirring continued for a period of up to about 60 minutes. After this time the mixture can be stripped of solvent to yield the desired product as the residue.

Exemplary compounds of formula VII useful for preparing the compounds of the present invention are hydroquinone, resorcinol, 4-methylresorcinol, 5-methylresorcinol, 2,5-dihydroxytoluene, 1,3-dihydroxy-4-chlorobenzene, 2-methyl-3-hydroxyphenol, 2-chloro-3-hydroxyphenol, 2-methyl-4-hydroxyphenol, 3-mercaptophenol, 4-mercaptophenol, 3-mercapto-5-methylphenol, 3-mercapto-5-bromophenol, 3-mercapto-5-iodophenol, 4-mercapto-5-chlorophenol and the like.

Exemplary compounds of formula VI useful for preparing the compounds of this invention are 1-chloro-2,2-dimethoxyethane, 1-chloro-2,2-diethoxyethane, 1-chloro-2,2-dipropoxyethane, 1-chloro-2,2-dibutoxyethane, 1-chloro-3,3-dimethoxypropane, 1-chloro-3,3-diethoxypropane, 1-chloro-3,3-dipropoxypropane and the like.

Exemplary suitable isocyanates of formula IV are methyl isocyanate, ethyl isocyanate, propyl isocyanate, butyl isocyanate, pentyl isocyanate, hexyl isocyanate, allyl isocyanate, but-3-enyl isocyanate, pent-4-enyl isocyanate, hex-4-enyl isocyanate, cyclopropyl isocyanate, cyclobutyl isocyanate, cyclopentyl isocyanate, cyclohexyl isocyanate, cycloheptyl isocyanate, phenyl isocyanate, 4-methylphenyl isocyanate, 3-chlorophenyl isocyanate, 3,4-dichlorophenyl isocyanate, 4-bromophenyl isocyanate, 4-fluorophenyl isocyanate, 4-iodophenyl isocyanate, 3-allylphenyl isocyanate, 4-hex-3-enylphenyl isocyanate, 2-methoxyphenyl isocyanate, 3-ethoxyphenyl isocyanate, 4-propoxyphenyl isocyanate, 3,5-dinitrophenyl isocyanate, 2-ethyl-4-chlorophenyl isocyanate, 3,4,5-trimethylphenyl isocyanate, 2-methylthiophenyl isocyanate, 4-t-butylphenyl isocyanate, benzyl isocyanate and the like.

Exemplary carbamoyl chlorides of formula III are methylcarbamoyl chloride, ethylcarbamoyl chloride, N,N-dimethylcarbamoyl chloride, N,N-diethylcarbamoyl chloride, N,N-dipropylcarbamoyl chloride, N-methyl-N-cyclopropylcarbamoyl chloride, N-methyl-N-phenylcarbamoyl chloride, N-ethyl-N-(3-chlorophenyl)carbamoyl chloride, N-methyl-N-(2,4,6-trichlorophenyl)carbamoyl chloride, N-methyl-N-benzylcarbamoyl chloride, N-allyl-N-(3-methylbenzyl)carbamoyl chloride and the like.

The manner in which the compounds of the present invention can be prepared is more specifically illustrated in the following examples.

EXAMPLE 1

Preparation of the Monosodium Salt of Hydroquinone

Hydroquinone (11.0 grams; 0.10 mole) and methanol (20 ml) were charged into a glass reaction vessel equipped with a mechanical stirrer and thermometer. The vessel was purged with nitrogen gas and sodium (2.3 grams) dissolved in methanol (30 ml) was added with continued stirring. After a period of about 15 minutes the reaction mixture was stripped of methanol under aspirator pressure to yield the desired product, the monosodium salt of hydroquinone as a white solid residue.

EXAMPLE 2

Preparation of 4-(2,2-Dimethoxyethoxy)phenol

The monosodium salt of hydroquinone prepared in Example 1 and dimethyl formamide (100 ml) were charged under nitrogen gas into a glass reaction vessel equipped with a mechanical stirrer, thermometer and addition funnel and were warmed to effect dissolution. The resulting solution was then allowed to warm to room temperature, and 1-chloro-2,2-dimethoxyethane was added dropwise over a period of about 20 minutes. After the addition was completed, the reaction mixture was heated at about 85° to 90° C. with stirring for a period of about 48 hours. After this time water (200 ml) was added, and the reaction mixture was neutralized with ammonium chloride. The reaction mixture was then extracted with chloroform, and the organic phase was separated from the aqueous phase. The organic phase was then stripped of solvent, leaving a red oil. This oil was distilled to yield the desired product 4-(2,2-dimethoxyethoxy)phenol as a pink oil boiling at 116° to 120° C. at 0.008 mm of Hg pressure.

EXAMPLE 3

Preparation of O-[4-(2,2-Dimethoxyethoxy)phenyl] N-Methylcarbamate 4-(2,2-Dimethoxyethoxy)phenol (5.0 grams) and benzene were charged into a glass reaction vessel equipped with a mechanical stirrer. Methyl isocyanate (3.5 ml) and 4 drops of triethylamine were then added, and the reaction mixture was stirred at room temperature for a period of about 6 hours. After this time the reaction mixture was filtered, and the filtrate was concentrated to 10 ml by partially stripping the solvent under reduced pressure. Cyclohexane (10 ml) was then added to the concentrate, resulting in the formation of a precipitate. The precipitate was recovered by filtration to yield the desired product O-[4-(2,2-dimethoxyethoxy)phenyl]

N-methylcarbamate as a slightly pink solid melting at 79° to 81° C.

EXAMPLE 4

Preparation of the Monosodium Salt of 5-Methylresorcinol

5-Methylresorcinol monohydrate (14.2 grams; 0.10 moles) dissolved in methanol (20 ml) was charged into a glass reaction vessel equipped with a mechanical stirrer and thermometer. The reaction mixture was blanketed with nitrogen gas, and sodium methoxide prepared by combining sodium (2.3 grams) with methanol (40 ml) was added with stirring. The reaction mixture was then heated at 50° C. with continued stirring for a period of about 15 minutes. After this time the reaction mixture was stripped of solvent under reduced pressure to yield the desired product as a grey solid.

EXAMPLE 5

Preparation of 3-(2,2-Dimethoxyethoxy)-5-hydroxytoluene

The monosodium salt of 5-methylresorcinol prepared in Example 4 and dimethyl formamide (200 ml) were charged under nitrogen gas into a glass reaction vessel equipped with a mechanical stirrer, thermometer and addition funnel. 1-Chloro-2,2-dimethoxyethane (6.25 grams) was added, and the mixture was heated at 85° to 90° C. and stirred for a period of about 22½ hours. After this time the reaction mixture was cooled to room temperature and was added to 1200 ml of water. The resulting mixture was carefully neutralized and extracted with chloroform. The organic phase was then separated from the aqueous phase and stripped of solvent, leaving a liquid residue. The residue was distilled under reduced pressure to yield a yellow viscous liquid which solidified upon cooling to −10° C. This product was then recrystallized from a methanol-water mixture, was washed with boiling water and dried to yield the desired product 3-(2,2-dimethoxyethoxy)-5-hydroxytoluene as a white solid melting at 73° to 75° C.

EXAMPLE 6

Preparation of O-[3-(2,2-Dimethoxyethoxy)-5-methylphenyl] N-Methylcarbamate 3-(2,2-Dimethoxyethoxy)-5-hydroxytoluene (2.50 grams), benzene (50 ml) and triethylamine (4 drops) were charged into a glass reaction vessel equipped with a mechanical stirrer. Methyl isocyanate (1.0 ml) was added to the vessel, and the resulting mixture was stirred at room temperature for a period of about 2 hours. The mixture was then allowed to stand at ambient temperature over the weekend. After this time the reaction mixture was stripped of benzene, leaving a viscous liquid residue. This residue was distilled under vacuum to yield the desired product O-[3-(2,2-dimethoxyethoxy)-5-methylphenyl] N-methylcarbamate as an oil.

EXAMPLE 7

Preparation of S-Sodium Salt of 3-Mercaptophenol

3-Mercaptophenol (3.15 grams) dissolved in methanol (5 ml) was charged into a glass reaction vessel equipped with a mechanical stirrer and thermometer. The reaction mixture was blanketed with nitrogen gas, and sodium methoxide, prepared by combining sodium (0.57 grams) and methanol (10 ml), was added with stirring. After the addition was completed, the mixture was heated with continued stirring for a period of about 15 minutes. After this time the reaction mixture was stripped of methanol under reduced pressure to yield the desired product S-sodium salt of 3-mercaptophenol as a semisolid residue.

EXAMPLE 8

Preparation of 3-(2,2-Dimethoxyethylthio)phenol

The S-sodium salt of 3-mercaptophenol prepared in Example 7 was dissolved in dimethylformamide (25 ml) and charged under nitrogen gas into a glass reaction vessel equipped with a mechanical stirrer, thermometer and addition funnel. The solution was heated to a temperature of 45 to 50° C., and 1-chloro-2,2-dimethoxyethane (3.15 grams) was added with stirring. After the addition was completed, stirring was continued for a period of about 3 hours. After this time the reaction mixture was poured into water (150 ml), and the resulting mixture was carefully neutralized with ammonium chloride. The mixture was then extracted with chloroform and the organic phase was separated. The organic portion was washed with water and then dried with phase separation paper. The dried solution was then stripped of solvent, leaving an oil. This oil was distilled, and the fraction boiling at 138° to 144° C. at 0.04 mm of Hg pressure was collected to yield the desired product 3-(2,2-dimethoxyethylthio)phenol.

EXAMPLE 9

Preparation of O-[3-(2,2-Dimethoxyethylthio)phenyl] N-Methylcarbamate 3-(2,2-Dimethoxyethylthio)phenol (1.80 grams) dissolved in benzene (5 ml) was charged into a glass reaction vessel equipped with a mechanical stirrer. Methyl isocyanate (12 ml) and trimethylamine (2 drops) were then added, and the resulting mixture was stirred at room temperature for a period of about 5½ hours. The mixture was then allowed to stand overnight and was then stripped of excess methyl isocyanate and a portion of the benzene. The concentrated solution was then added to ether and cooled to −60° C., resulting in a precipitate. The precipitate was recrystallized from ether to yield the desired product O-[3-(2,2-dimethoxyethylthio)phenyl]-0 N-methylcarbamate having a melt point of 46° to 48° C.

EXAMPLE 10

Preparation of the Monosodium Salt of Resorcinol

Resorcinol (0.10 mole) and methanol (20 ml) are charged into a glass reaction vessel equipped with a mechanical stirrer and thermometer. Sodium (0.10 mole) dissolved in methanol (30 ml) is then added under nitrogen gas to the reaction vessel with continued stirring. After a period of about 15 minutes the reaction mixture is stripped of methanol under aspirator pressure to yield the desired product the monosodium salt of resorcinol as the residue.

EXAMPLE 11

Preparation of 4-(3,3-Dimethoxypropoxy)phenol

The monosodium salt of hydroquinone (0.05 mole) and dimethylformamide (75 ml) are charged under nitrogen gas into a glass reaction vessel equipped with a mechanical stirrer, thermometer and addition funnel.

The mixture is stirred until dissolved, and 1-chloro-3,3-dimethoxypropane (0.05 mole) is added dropwise over a period of about 20 minutes. After the addition is completed, the reaction mixture is heated at about 90° C. with stirring for a period of about 48 hours. After this time water (200 ml) is added, and the reaction mixture is carefully neutralized with ammonium chloride. The reaction mixture is then extracted with chloroform, and the organic phase is separated from the aqueous phase. The organic phase is then stripped of solvent, leaving an oil. This oil is distilled under reduced pressure to yield the desired product 4-(3,3-dimethoxypropoxy)phenol.

EXAMPLE 12

Preparation of O-[4-(3,3-Dimethoxypropoxy)phenyl] N-Allylcarbamate 4-(3,3-Dimethoxypropoxy)phenol (0.05 mole) dissolved in benzene (10 ml) is charged into a glass reaction flask equipped with a mechanical stirrer. Allyl isocyanate (0.06 mole) and triethylamine (3 drops) are then added, and the resulting mixture is stirred at room temperature for a period of about 6 hours. The dried solution is stirpped of solvent and unreacted isocyanate to yield the desired product O-[4-(3,3-dimethoxypropoxy)phenyl] N-allylcarbamate as the residue.

EXAMPLE 13

Preparation of 3-(2,2-Diethoxyethoxy)-5-chlorophenol

The monosodium salt of 3-hydroxy-5-chlorophenol (0.05 mole) and dimethylformamide (75 ml) are charged under nitrogen gas into a glass reacton vessel equipped with a mechanical stirrer, thermometer and addition funnel. The mixture is stirred until dissolved, and 1-chloro-2,2-diethoxyethane (0.05 mole) is added dropwise over a period of about 20 minutes. After the addition is completed, the reaction mixture is heated at about 90° C. with stirring for a period of about 48 hours. After this time water (200 ml) is added, and the reaction mixture is neutralized with ammonium chloride. The reaction mixture is then extracted with chloroform, and the organic phase is separated from the aqueous phase. The organic phase is then stripped of solvent, leaving an oil. This oil is distilled under reduced pressure to yield the desired product 3-(2,2-diethoxyethoxy)-5-chlorophenol.

EXAMPLE 14

Preparation of O-[3-(2,2-Diethoxyethoxy)-5-chlorophenyl] N-Phenylcarbamate 3-(2,2-Diethoxyethoxy)-5-chlorophenol (0.05 mole) dissolved in benzene (10 ml) is charged into a glass reaction flask equipped with a mechanical stirrer. Phenyl isocyanate (0.06 mole) and triethylamine (3 drops) are then added, and the resulting mixture is stirred at room temperature for a period of about 6 hours. The mixture is then stripped of solvent and unreacted isocyanate to yield the desired product O-[3-(2,2-diethoxyethoxy)-5-chlorophenyl] N-phenylcarbamate as the residue.

EXAMPLE 15

Preparation of 3-(2,2-Dimethoxyethoxy)-5-bromophenol

The monosodium salt of 3-hydroxy-5-bromophenol (0.05 mole) and dimethylformamide (75 ml) are charged under nitrogen gas into a glass reaction vessel equipped with a mechanical stirrer, thermometer and additional funnel. The mixture is stirred until dissolved, and 1-chloro-2,2-dimethoxyethane (0.05 mole) is added dropwise over a period of about 20 minutes. After the addition is completed, the reaction mixture is heated at about 90° C. with stirring for a period of about 48 hours. After this time water (200 ml) is added, and the reaction mixture is neutralized with ammonium chloride. The reaction mixture is then extracted with chloroform, and the organic phase is separated from the aqueous phase. The organic phase is then stripped of solvent, leaving an oil. This oil is distilled under reduced pressure to yield the desired product 3-(2,2-dimethoxyethoxy)-5-bromophenol.

EXAMPLE 16

Preparation of O-[3-(2,2-Dimethoxyethoxy)-5-bromophenyl] N-2-Methylphenylcarbamate 3-(2,2-Dimethoxyethoxy)-5-bromophenol (0.05 mole) dissolved in benzene (10 ml) is charged into a glass reaction flask equipped with a mechanical stirrer. 2-Methylphenyl isocyanate (0.06 mole) and triethylamine (3 drops) are then added, and the resulting mixture is stirred at room temperature for a period of about 6 hours. The mixture is then stripped of solvent and unreacted isocyanate to yield the desired product O-[3-(2,2-dimethoxyethoxy)-5-bromophenyl] N-2-methylphenylcarbamate as the residue.

EXAMPLE 17

Preparation of 4-(2,2-Dipropoxyethylthio)phenol

The S-monosodium salt of 4-mercaptophenol (0.05 mole) and dimethylformamide (75 ml) are charged into a glass reaction vessel equipped with a mechanical stirrer, thermometer and addition funnel. The mixture is stirred until dissolved, and 1-chloro-2,2-dipropoxyethane (0.05 mole) is added dropwise over a period of about 20 minutes. After the addition is completed, the reaction mixture is blanketed with nitrogen gas and is heated at about 90° C. with stirring for a period of about 48 hours. After this time water (200 ml) is added, and the reaction mixture is neutralized with ammonium chloride. The reaction mixture is then extracted with chloroform, and the organic phase is separated from the aqueous phase. The organic phase is then stripped of solvent, leaving an oil. This oil is distilled under reduced pressure to yield the desired product 4-(2,2-dipropoxyethylthio)phenol.

EXAMPLE 18

Preparation of O-[4-(2,2-Dipropoxyethylthio)phenyl] N-Cyclopropylcarbamate 4-(2,2-Dipropoxyethylthio)phenol (0.05 mole) dissolved in benzene (10 ml) is charged into a glass reaction flask equipped with a mechanical stirrer. Cyclopropylisocyanate (0.06 mole) and triethylamine (3 drops) are then added, and the resulting mixture is stirred at room temperature for a period of about 6 hours. The mixture is then stripped of solvent and unreacted isocyanate to yield the desired product O-[4-(2,2-dipropoxyethylthio)phenyl] N-cyclopropylcarbamate as the residue.

EXAMPLE 19

Preparation of O-[4-(2,2-Dimethoxyethoxy)phenyl] N-3-Allylphenylcarbamate 4-(2,2-Dimethoxyethoxy)phenol (0.05 mole) dissolved in benzene (10 ml) is charged into a glass reaction flask equipped with a mechanical stirrer. 3-Allylphenyl isocyanate (0.06 mole) and triethylamine (3 drops) are then added, and the resulting mixture is stirred at room temperature for a period of about 6 hours. The mixture is stripped of solvent and unreacted isocyanate to yield the desired product O-[4-(2,2-dimethoxyethoxy)phenyl] N-3-allylphenylcarbamate as the residue.

EXAMPLE 20

Preparation of O-[4-(2,2-Dimethoxyethoxy)phenyl] N-4-Methoxyphenylcarbamate 4-(2,2-Dimethoxyethoxy)phenol (0.05 mole) dissolved in benzene (10 ml) is charged into a glass reaction flask equipped with a mechanical stirrer. 4-Methoxyphenyl isocyanate (0.06 mole) and triethylamine (3 drops) are then added, and the resulting mixture is stirred at room temperature for a period of about 6 hours. The mixture is then stripped of solvent and unreacted isocyanate to yield the desired product O-[4-(2,2-dimethoxyethoxy)phenyl] N-4-methoxyphenylcarbamate as the residue.

EXAMPLE 21 preparation of O-[4-(2,2-Dimethoxyethoxy)phenyl] N-3,4-Dichlorophenylcarbamate 4-(2,2-Dimethoxyethoxy)phenol (0.05 mole) dissolved in benzene (10 ml) is charged into a glass reaction flask equipped with a mechanical stirrer. 3,4-Dichlorophenyl isocyanate (0.06 mole) and triethylamine (3 drops) are then added, and the resulting mixture is stirred at room temperature for a period of about 6 hours. The mixture is then stripped of solvent and unreacted isocyanate to yield the desired product O-[4-(2,2-dimethoxyethoxy)phenyl] N-3,4-dichlorophenylcarbamate as the residue.

EXAMPLE 22

Preparation of O-[3-(2,2-Dimethoxyethylthio)phenyl] N-Cyclohexylcarbamate 3-(2,2-Dimethoxyethylthio)phenol (0.05 mole) dissolved in benzene (10 ml) is charged into a glass reaction flask equipped with a mechanical stirrer. Cyclohexyl isocyanate (0.06 mole) and triethylamine (3 drops) are then added, and the resulting mixture is stirred at room temperature for a period of about 6 hours. The mixture is then stripped of solvent and unreacted isocyanate to yield the desired product O-[3-(2,2-dimethoxyethylthio) phenyl] N-cyclohexylcarbamate as the residue.

EXAMPLE 23

Preparation of O-[3-(2,2-Dimethoxyethylthio)phenyl] N-3-Nitrophenylcarbamate 3-(2,2-Dimethoxyethylthio)phenol (0.05 mole) dissolved in benzene (10 ml) is charged into a glass reaction flask equipped with a mechanical stirrer. 3-Nitrophenyl isocyanate (0.06 mole) and triethylamine (3 drops) are then added and the resulting mixture is stirred at room temperature for a period of about 6 hours. The mixture is then stripped of solvent and unreacted isocyanate to yield the desired product O-[3-(2,2-dimethoxyethylthio) phenyl] N-3-nitrophenylcarbamate as the residue.

EXAMPLE 24

Preparation of O-[3-(2,2-Dimethoxyethylthio)phenyl] N-4-Methylthiophenylcarbamate 3-(2,2-Dimethoxyethylthio)phenol (0.05 mole) dissolved in benzene (10 ml) is charged into a glass reaction flask equipped with a mechanical stirrer. 4-Methylthiophenyl isocyanate (0.06 mole) and triethylamine (3 drops) are then added, and the resulting mixture is stirred at room temperature for a period of about 6 hours. The mixture is then stripped of solvent and unreacted isocyanate to yield the desired product O-[3-(2,2-dimethoxyethylthio)-phenyl] N-4-methylthiophenylcarbamate as the residue.

EXAMPLE 25

Preparation of O-[3-(2,2-Dimethoxyethoxy)-5-methylphenyl] N,N-Dimethylcarbamate 3-(2,2-Dimethoxyethoxy)-5-methylphenol (0.05 mole), N,N-dimethylcarbamoyl chloride (0.08 mole), triethylamine (0.05 mole) and xylene (50 ml) are charged into a glass reaction flask equipped with a mechanical stirrer, thermometer and reflux condenser. The mixture is stirred and heated at 80° C. for a period of about 12 hours. After this time the reaction mixture is cooled to room temperature and is filtered. The filtrate is then washed with water and dried over anhydrous magnesium sulfate. The dried solution is then filtered and stripped of solvent and unreacted starting materials to yield the desired product O-[3-(2,2-dimethoxyethoxy)-5-methylphenyl] N,N-dimethylcarbamate as the residue.

EXAMPLE 26

Preparation of O-[4-(2,2-Dimethoxyethoxy)phenyl] N-Methyl-N-cyclopropylcarbamate 4-(2,2-Dimethoxyethoxy)phenol (0.05 mole), N-methyl-N-cyclopropylcarbamoyl chloride (0.08 mole), triethylamine (0.05 mole) and xylene (50 ml) are charged into a glass reaction flask equipped with a mechanical stirrer, thermometer and reflux condenser. The mixture is stirred and heated at 80° C. for a period of about 12 hours. After this time the reaction mixture is cooled to room temperature and is filtered. The filtrate is then washed with water and dried over anhydrous magnesium sulfate. The dried solution is then filtered and stripped of solvent and unreacted starting materials to yield the desired product O-[4-(2,2-dimethoxyethoxy)phenyl] N-methyl-N-cyclopropylcarbamate as the residue.

EXAMPLE 27

Preparation of O-[4-(2,2-Dimethoxyethoxy)phenyl] N-Ethyl-N-3,4-dibromophenylcarbamate 4-(2,2-Dimethoxyethoxy)phenol (0.05 mole), N-ethyl-N-3,4-dibromophenylcarbamoyl chloride (0.08 mole), triethylamine (0.05 mole) and xylene (50 ml) are charged into a glass reaction flask equipped with a mechanical stirrer, thermometer and reflux condenser. The mixture is stirred and heated at reflux for a period of about 12 hours. After this time the reaction mixture is cooled to room temperature and is filtered. The filtrate is then washed with water and dried over anhydrous magnesium sulfate. The dried solution is then filtered and stripped of solvent and unreacted starting materials to yield the desired product O-[4-(2,2-dimethoxyethoxy)phenyl] N-ethyl-N-3,4-dibromophenylcarbamate as the residue.

EXAMPLE 28

Preparation of O-[4-(2,2-Dimethoxyethoxy)phenyl] N-Allyl-N-benzylcarbamate 4-(2,2-Dimethoxyethoxy)phenol (0.05 mole), N-allyl-N-benzylcarbamoyl chloride (0.08 mole), triethylamine (0.05 mole) and xylene (50 ml) are charged into a glass reaction flask equipped with a mechanical stirrer, thermometer and reflux condenser. The mixture is stirred and heated at reflux for a period of about 12 hours. After this time the reaction mixture is cooled to room temperature and is filtered. The filtrate is then washed with water and dried over anhydrous magnesium sulfate. The dried solution is then filtered and stripped of solvent and unreacted starting materials to yield the desired product O-[4-(2,2-dimethoxyethoxy)phenyl] N-allyl-N-benzylcarbamate as the residue.

Other compounds of the present invention can be prepared readily by the procedures described above. Presented in the following examples are the essential reactants required to prepare the indicated named compounds according to the methods heretofore described.

EXAMPLE 29

4-Mercaptophenol+sodium methoxide+1-chloro-2,2-dimethoxyethane+methyl isocyanate=O-[4-2,2-dimethoxyethylthio)phenyl] N-methylcarbamate; m.p. 51° to 52° C.

EXAMPLE 30

3-Hydroxy-5-methylphenol+sodium methoxide+1-chloro-2,2-diethoxyethane+methyl isocyanate=O-[3-(2,2-diethoxyethoxy)-5-methyl] N-methylcarbamate; m.p. 67° to 69° C.

EXAMPLE 31

2-Methyl-3-hydroxyphenol+sodium methoxide+1-chloro-2,2-dimethoxyethane+methyl isocyanate=O-[3-(2,2-dimethoxyethoxy)-2-methyl] N-methylcarbamate; m.p. 53° to 56° C.

EXAMPLE 32

3-Hydroxy-5-chlorophenol+sodium methoxide+1-chloro-2,2-dimethoxyethane+methyl isocyanate=O-[3-(2,2-dimethoxyethoxy)-5-chlorophenyl] N-methylcarbamate.

EXAMPLE 33

3-Mercapto-5-methylphenol+sodium methoxide+1-chloro-2,2-dimethoxyethane+methyl isocyanate=O-[3-(2,2-dimethoxyethylthio)-5-methylphenyl] N-methylcarbamate.

Additional compounds within the scope of this invention which can be prepared according to the details of the foregoing examples include O-[3-(2,2-dimethoxyethoxy)-4-methylphenyl] N-ethylcarbamate, O-[3-(2,2-diethoxyethoxy)-5-ethylphenyl] N-propylcarbamate, O-[3-(2,2-dipropoxyethoxy)-5-propylphenyl] N-butylcarbamate, O-[3-(2,2-dibutoxypropoxy)-5-butylphenyl] N-pentylcarbamate, O-[3-(2,2-dipentyloxyethoxy)-5-pentylphenyl] N-hexylcarbamate, O-[3-(2,2-dihexyloxyethoxy)-5-hexylphenyl] N,N-dimethylcarbamate, O-[3-(2,2-dimethoxyethoxy)-5-iodophenyl] N,N-diethylcarbamate, O-[3-(2,2-dimethoxyethoxy)-5-fluorophenyl] N,N-dipropylcarbamate, O-[3-(2-methoxy-2-ethoxyethoxy)-5-methylphenyl] N,N-dibutylcarbamate, O-[3-(2-methoxy-2-propoxyethoxy)-5-methylphenyl] N,N-dipentylcarbamate, O-[3-(2-methoxy-2-ethoxypropoxy)-5-methylphenyl] N,N-dihexylcarbamate, O-[4-(2,2-dimethoxypropylthio)phenyl] N-cyclobutylcarbamate, O-[4-(2,2-dipropoxypropylthio)phenyl] N-cyclopentylcarbamate, O[4-(2,2-dibutyloxypropylthio)phenyl] N-cyclohexylcarbamate, O-[4-(2,2-dipentyloxypropylthio)phenyl] N-cycloheptylcarbamate, O-[4-(2,2-dihexyloxypropylthio)phenyl] N,N-diethylcarbamate, O-[4-(2,2-dimethoxyethylthio)phenyl] N,N-dipropylcarbamate, O-[4-(2,2-diethoxyethylthio)phenyl] N,N-dibutylcarbamate, O-[4-(2,2-dipropoxyethylthio)phenyl] N,N-dipentylcarbamate, O-[4-(2,2-dibutoxyethylthio)phenyl] N,N-dihexylcarbamate, O-[4-(2,2-dipentyloxyethylthio)phenyl] N-but-3-enylcarbamate, O-[4-(2,2-dihexyloxyethylthio)phenyl] N-pent-4-enylcarbamate, O-[3-(2,2-dimethoxyethoxy)phenyl] N-hex-4-enylcarbamate, O-[3-(2,2-dimethoxyethoxy)phenyl] N-3-ethylphenylcarbamate, O-[3-(2,2-dimethoxyethoxy)phenyl] N-4-propylphenylcarbamate, O-[3-(2,2-dimethoxyethoxy)phenyl] N-3-butylphenylcarbamate, O-[3-(2,2-dimethoxyethoxy)phenyl] N-4-pentylphenylcarbamate, O-[3-(2,2-dimethoxyethoxy)phenyl] N-4-hexylphenylcarbamate, O-[3-(2,2-dimethoxyethoxy)phenyl] N-3-but-3-enylphenylcarbamate, O-[3-(2,2-dimethoxyethoxy)phenyl] N-4-hex-4-enylphenylcarbamate, O-[3-(2,2-dimethoxyethoxy)phenyl] N-2-ethoxyphenylcarbamate, O-[3-(2,2-dimethoxyethoxy)phenyl] N-3-propoxyphenylcarbamate, O-[3-(2,2-dimethoxyethoxy)phenyl] N-4-pentyloxyphenylcarbamate, O-[3-(2,2-dimethoxyethoxy)phenyl] N-4-hexyloxyphenylcarbamate, O-[3-(2,2-dimethoxyethoxy)phenyl] N-3,4-dichlorophenylcarbamate, O-[3-(2,2-dimethoxyethoxy)-phenyl] N-4-fluorophenylcarbamate, O-[3-(2,2-dimethoxyethoxy)-phenyl] N-4-iodophenylcarbamate, O-[3-(2,2-dimethoxyethoxy)-phenyl] N-4-bromophenylcarbamate, 0-[3-(2,2-dimethoxyethoxy)-phenyl] N-4-ethylthiophenylcarbamate, O-[3-(2,2-dimethoxyethoxy)phenyl] N-4-propylthiophenylcarbamate, O-[3-(2,2-dimethoxyethoxy)phenyl] N-4-hexylthiophenylcarbamate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 34

Preparation of a Dust

| | |
|---|---|
| Product of Example 3 | 10 |
| Powdered talc | 90 |

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesive, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, ethion, parathion, methyl parathion, EPN, demeton, carbophenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-o-cresol, dinitrocyclohexylphenol, DNB, DNP, binapacril, azobenzene and the like; organic carbamate compounds such as carbaryl, ortho 5353 and the like; organic sulfur compounds such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig border and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of the present invention was demonstrated by experiments carried out for the control of a variety of insects.

Housefly

Approximately 25 to 30 four-day-old Housefly adults are placed in spherical wire mesh cages. The cages are mounted at the center of a rotating turntable so that each cage rotates on its own axis. At least three cages are provided for each test unit. Individual rotating cages are sprayed with aerosol formulations of the test compound at the indicated concentrations. Houseflies are then immediately removed to observation cages, observed for 60-minute knockdown, supplied sugar-water food source, transferred to a holding room and observed for mortality 24 hours after treatment. The results of this test are shown in Table I.

TABLE I

| Test Compound | Rate (ppm): | 1024 | 512 | 256 | 128 | 64 | 32 | 16 | 8 |
|---|---|---|---|---|---|---|---|---|---|
| Product of Example 3 | k | — | 50 | 10 | 0 | 0* | 0 | 0 | 0 |
|  | m | — | 60 | 40 | 30 | 0* | 0 | 0 | 0 |
| Product of Example 6 | k | 100 | 100 | 70 | 40 | 0 | 0 | 0 | 0 |
|  | m | 100 | 80 | 100 | 100 | 10 | 0 | 0 | 10 |
| Product of Example 9 | k | — | 100 | 100 | 70 | 25* | 0 | 0 | 0 |
|  | m | — | 100 | 100 | 100 | 60* | 0 | 0 | 0 |
| Product of Example 29 | k | 100 | 90 | 60 | 40 | — | — | — | — |
|  | m | 100 | 90 | 60 | 40 | — | — | — | — |
| Product of Example 30 | k | 100 | 100 | 100 | 30 | 0 | 10 | 0 | 0 |
|  | m | 100 | 100 | 100 | 90 | 90 | 30 | 20 | 0 |
| Product of Example 31 | k | 100 | 100 | 90 | 40 | 20 | — | — | — |
|  | m | 100 | 100 | 100 | 40 | 50 | — | — | — |
| Product of Example 32 | k | 100 | 100 | 0 | 0 | 70 | — | — | — |
|  | m | 100 | 100 | 90 | 90 | 70 | — | — | — |
| Product of Example 33 | k | 100 | 100 | 100 | 100 | 40 | — | — | — |
|  | m | 100 | 90 | 20 | 70 | 0 | — | — | — | k = 60-minute knockdown
m = 24-hour mortality
*Values are averages of two replicates.

Southern Armyworm

Foliar portions of potted Dwarf Horticultural bean plants in first true leaf growth stage are sprayed with test solution containing a compound of this invention. The pots are then placed in holding racks provided with a subterranean water source. Three test plants are used for each test unit. Five third-instar larvae of Southern Armyworm are caged on treated plants for 48 hours. After this time observations are made for insect mortality. The results of this procedure are set forth in Table II.

TABLE II

| Test Compound Rate (ppm): | Percent Control | | | | |
|---|---|---|---|---|---|
|  | 1024 | 512 | 256 | 128 | 64 |
| Product of Example 3 | — | 10 | 0 | 0 | 0 |
| Product of Example 6 | 0 | 0 | 0 | 0 | — |
| Product of Example 9 | — | 0 | 0 | 0 | 0 |
| Product of Example 29 | 0 | 0 | 0 | 0 | — |
| Product of Example 30 | 0 | 30 | 10 | 30 | 0 |
| Product of Example 31 | 0 | 0 | 0 | 0 | 0 |
| Product of Example 32 | 20 | 10 | 10 | 30 | — |
| Product of Example 33 | 100 | 80 | 0 | 0 | 0 |

Mexican Bean Beetle

Foliar portions of potted Dwarf Horticultural bean plants in first true leaf growth stage are sprayed with test solution containing a compound of this invention, and in some cases the soil of the potted plants is also drenched with an aqueous emulsion of the test compound. The pots are then placed in holding racks provided with a subterranean water source. Three test plants are used for each test unit. Five third-instar larvae of Mexican Bean Beetle are caged on treated plants for 48 hours. After this time observations are made for insect mortality. The results of these experiments are summarized in Table III.

TABLE III

| Test Compound | Percent Control Rate (ppm) | | | | | | | |
|---|---|---|---|---|---|---|---|---|
|  | 1024 | 512 | 256 | 128 | 64 | 32 | 16 | 8 |
| Product of Example 3 | — | 0 | 0 | 0 | 10 | — | — | — |
| +64 #/acre soil drench | — | 10 | 0 | 10 | 20 | — | — | — |
| Product of Example 6 | 10 | 10 | 10 | 0 | — | — | — | — |
| Product of Example 9 | — | 30 | 20 | 10 | 0 | — | — | — |
| Product of Example 29 | 50 | 30 | 10 | 0 | — | — | — | — |
| Product of Example 30 | 100 | 100 | 100 | 90 | 100 | 20 | 20 | 10 |
| Product of Example 31 | 100 | 100 | 100 | 90 | 70 | — | — | — |
| Product of Example 32 | 80 | 90 | 90 | 30 | 0 | — | — | — |
| Product of Example 33 | 100 | 100 | 100 | 90 | 100 | 90 | 80 | 50 |

Boll Weevil

Two leaves of a cotton plant are sprayed with test solution containing a compound of this invention at the indicated rates and are allowed to air dry. Boll weevils are then placed on the surface of the leaves, and the infested leaves are kept in a petri dish and are held for a period of 48 hours. After this time mortality is observed and compared to untreated controls. The results of these tests are shown in Table IV.

TABLE IV

| Test Compound | Percent Control Rate (ppm) | | | | | | | |
|---|---|---|---|---|---|---|---|---|
| | 1024 | 512 | 256 | 128 | 64 | 32 | 16 | 8 |
| Product of Example 3 | — | 80 | 50 | 40 | 30 | — | — | — |
| Product of Example 6 | — | 0 | 10 | 0 | 0 | — | — | — |
| Product of Example 9 | — | 40 | 20 | 20 | 10 | — | — | — |
| Product of Example 29 | 0 | 0 | 0 | 0 | — | — | — | — |
| Product of Example 30 | 10 | 30 | 20 | 10 | 10 | — | — | — |
| Product of Example 31 | 40 | 30 | 20 | 20 | 20 | 20 | 10 | 10 |
| Product of Example 32 | 0 | 10 | 10 | 30 | — | — | — | — |
| Product of Example 33 | 70 | 50 | 40 | 30 | 20 | — | — | — |

Two-Spotted Spider Mite

Potted horticultural beans at growth stage when primary leaves are approximately one inch long are infested with two-spotted spider mites 24 hours prior to treatment, ensuring establishment of adults and egg deposition at time of treatment.

The candidate compound is dissolved in a suitable solvent (acetone, methanol or other) or prepared as a wettable powder and diluted to appropriate concentrations with deionized water containing wetting and/or dispersing agents as appropriate.

Infested host plants, as above, are sprayed with test solution containing a compound of this invention. The pots are then placed in holding racks provided with a subterranean water source. Mortality is determined 48 hours after treatment by removing and observing one leaf from each plant. The results of these tests are set forth in Table V.

TABLE V

| Test Compound | Percent Control Rate (ppm) | | | | |
|---|---|---|---|---|---|
| | 1024 | 512 | 256 | 128 | 64 |
| Product of Example 3 | 0 | 0 | 0 | 0 | — |
| Product of Example 9 | 80 | 60 | 0 | 0 | — |
| Product of Example 29 | 30 | 20 | 0 | 0 | — |
| Product of Example 30 | 85 | 88 | 90 | 80 | 83 |
| Product of Example 31 | 85 | 84 | 90 | 80 | 0 |
| Product of Example 32 | 92 | 96 | 90 | 80 | 20 |
| Product of Example 33 | 95 | 90 | 60 | 50 | 20 |

Cabbage Looper

Ten- to fourteen-day-old Henderson bush lima bean plants are planted in 3½" plastic pots using potting soil capped with ¼" of sand. The bean plants are then placed on a turntable and are sprayed with 100 ml of an aqueous solution or dispersion of a compound of this invention at the indicated concentrations. The plants are allowed to dry, and a leaf is removed from each and placed in a petri dish on top of a piece of wetted filter paper. Ten third-instar larvae of the Cabbage Looper are then placed on the leaf, and the petri dish is covered. Observations of mortality are made after 48 hours and are compared to untreated controls. Results of these tests are shown in Table VI.

TABLE VI

| Test Compound Rate (ppm): | Percent Control | | | | |
|---|---|---|---|---|---|
| | 1024 | 512 | 256 | 128 | 64 |
| Product of Example 3 | — | 70 | 50 | 30 | 10 |
| Product of Example 6 | 30 | 0 | 0 | 10 | — |
| Product of Example 9 | — | 100 | 90 | 80 | 80 |
| Product of Example 29 | 0 | 0 | 0 | 0 | — |
| Product of Example 30 | 60 | — | — | — | 10 |
| Product of Example 31 | 30 | — | — | — | 10 |
| Product of Example 32 | 20 | 10 | 10 | 10 | 30 |

Yellow Fever Mosquito Larvae

Aliquots of 100 ml of tap water containing various concentrations of compounds of this invention are each supplied with 20 1-day-old Yellow Fever Mosquito larvae (*Aedes aegypti* L.). The larvae are maintained at 25° C. and are fed with malt yeast powder. After 13 days, when the pupae of untreated insects have hatched, the mortality percentages are calculated in comparison with the untreated controls. The results are indicated in Table VII.

TABLE VII

| Test Compound | Percent Control Rate (ppm): | | | | | | | | |
|---|---|---|---|---|---|---|---|---|---|
| | 512 | 128 | 32 | 10 | 8 | 2 | 1 | 0.1 | 0.01 |
| Product of Example 3 | 100 | 80 | 60 | 80 | 10 | 0 | 70 | 50 | 30 |
| Product of Example 6 | — | — | — | 100 | — | — | 40 | 0 | 0 |
| Product of Example 9 | 100 | 100 | 100 | 100 | 50 | 30 | 70 | 20 | 0 |
| Product of Example 29 | — | — | — | 100 | — | — | 40 | 0 | 0 |
| Product of Example 30 | — | — | — | 20 | — | — | 10 | 10 | 10 |
| Product of Example 31 | — | — | — | 40 | — | — | 20 | 0 | 0 |
| Product of Example 32 | — | — | — | 10 | — | — | 10 | 0 | 0 |
| Product of Example 33 | — | — | — | 100 | — | — | 90 | 60 | 40 |

Pea Aphid

Windsor Broad Bean plants grown under greenhouse conditions, in the first true leaf growth stage and in soil of low moisture content are sprayed with test solution containing a compound of this invention. The pots are then placed in holding racks provided with a subterranean water source. Adult pea aphids are transferred to the foliar portion of the treated plants and held there for a period of 48 hours. After this time insect mortality is determined by observation in comparison to controls. The results of these procedures are shown in Table VIII.

TABLE VIII

| Test Compound Rate (ppm): | Percent Control | | | | |
|---|---|---|---|---|---|
| | 1024 | 512 | 256 | 128 | 64 |
| Product of Example 3 | | 35 | 35 | 20 | 10 | — |

TABLE VIII-continued

| Test Compound | Rate (ppm): | Percent Control |  |  |  |  |
|---|---|---|---|---|---|---|
| | | 1024 | 512 | 256 | 128 | 64 |
| Product of Example 6 | | 100 | 100 | 100 | 90 | — |
| Product of Example 9 | | 80 | 60 | 60 | 50 | — |
| Product of Example 29 | | 70 | 40 | 0 | 0 | — |
| Product of Example 30 | | 0 | 0 | 0 | 0 | — |
| Product of Example 31 | | 0 | 0 | 0 | 0 | — |
| Product of Example 32 | | 0 | 0 | 0 | 0 | — |
| Product of Example 33 | | 100 | 100 | 50 | 25 | 0 |

Green Peach Aphid

Dwarf Masturtiums are planted in 3½" plastic pots containing potting soil capped with ¼" of sand. Ten- to fourteen-day-old plants are placed on a revolving table in a mist chamber and sprayed with 100 ml of a solution containing a compound of this invention at the indicated concentrations. After the leaves have dried, an untreated leaf infested with 10 to 20 Green Peach Aphids is placed on a treated leaf. As the untreated leaf wilts, the aphids crawl onto the treated leaf. Mortality is recorded in comparison to untreated controls 48 hours after infestation of the treated plant. The results of these tests are set forth in Table IX.

TABLE IX

| Test Compound | Percent Control Rate (ppm) |  |  |  |  |  |  |  |
|---|---|---|---|---|---|---|---|---|
| | 1024 | 512 | 256 | 128 | 64 | 32 | 16 | 8 |
| Product of Example 3 | 35 | 0 | 0 | 0 | — | — | — | — |
| Product of Example 6 | 100 | 100 | 100 | 80 | — | — | — | — |
| Product of Example 9 | 100 | 100 | 75 | 10 | — | — | — | — |
| Product of Example 29 | 0 | 0 | 0 | 0 | — | — | — | — |
| Product of Example 30 | 96 | 85 | 40 | 40 | 30 | — | — | — |
| Product of Example 31 | 100 | 100 | 90 | 75 | 0 | — | — | — |
| Product of Example 32 | 100 | 90 | 80 | 60 | 75 | — | — | — |
| Product of Example 33 | 90 | 90 | 50 | 25 | 0 | 100 | 40 | 10 |

German Cockroach

Ten adult German cockroaches are first anesthetized with carbon dioxide and thereafter dipped into a 100 ml solution of the test compound at the indicated concentrations. Thereafter the cockroaches are placed in holding cups and supplied with water as required. Mortality of the roaches is observed 48 hours after treatment in comparison to untreated controls. The results of these tests are shown in Table X.

TABLE X

| Test Compound | Rate (ppm): | Percent Control |  |  |  |
|---|---|---|---|---|---|
| | | 1024 | 512 | 256 | 128 |
| Product of Example 3 | | 20 | 10 | 10 | 0 |
| Product of Example 6 | | 100 | 40 | 10 | 0 |
| Product of Example 9 | | 70 | 20 | 10 | 0 |

The systemic activity of the compounds of the present invention was demonstrated in experiments wherein the test compounds were applied as soil drenches. In the soil drench applications fourteen-day-old cotton plants or bean plants are watered with 25 ml of a solution of the test compound at the indicated rates. After 48 hours the primary leaves are removed and placed in a closed container with the insect species. For those species of insects which do not leave their host plants the insects are placed on the growing plants. In each instance forty-eight hours after infestation mortality was observed and compared to untreated controls. The results of these tests are shown in Table XI.

TABLE XI

| Product of Examples: | Insect Species | | SOIL DRENCH Rate #/A Percent Control | | | | | | | |
|---|---|---|---|---|---|---|---|---|---|---|
| | | | 64 | 32 | 16 | 8 | 4 | 2 | 1 | .5 |
| 30 | SAW | | 10 | — | — | — | — | — | — | — |
| " | MBB | | 30 | — | — | — | — | — | — | — |
| " | TSM | | 50 | — | — | — | — | — | — | — |
| " | CAL | | 20 | — | — | — | — | — | — | — |
| " | GPA | | 60 | — | — | — | — | — | — | — |
| " | SCR | 24h | — | — | 80 | 80 | 80 | 60 | 40 | — |
| | | 48h | — | — | 100 | 100 | 100 | 80 | 60 | — |
| 31 | SAW | | 20 | — | — | — | — | — | — | — |
| " | MBB | | 90 | 100 | 90 | 100 | 30 | 10 | 10 | — |
| " | TSM | | 60 | 40 | 20 | 0 | — | — | — | — |
| " | CAL | | 20 | — | — | — | — | — | — | — |
| " | PA | | — | — | — | — | 80 | 60 | 50 | 0 |
| " | GPA | | 100 | 100 | 100 | 90 | 90 | 50 | 40 | — |
| " | SCR | 24h | — | — | 80 | 80 | 60 | 40 | 20 | — |
| | | 48h | — | — | 100 | 100 | 100 | 80 | 60 | — |
| 32 | SAW | | 30 | — | — | — | — | — | — | — |
| " | MBB | | 30 | — | — | — | — | — | — | — |
| " | BW | | 0 | — | — | — | — | — | — | — |
| " | TSM | | 0 | — | — | — | — | — | — | — |
| " | CAL | | 10 | — | — | — | — | — | — | — |
| " | GPA | | 50 | — | — | — | — | — | — | — |
| " | SCR | 24h | — | — | 100 | 100 | 100 | 80 | 40 | — |

TABLE XI-continued

| Product of Examples: | Insect Species | | SOIL DRENCH Rate #/A | | | | | | | |
|---|---|---|---|---|---|---|---|---|---|---|
| | | | Percent Control | | | | | | | |
| | | | 64 | 32 | 16 | 8 | 4 | 2 | 1 | .5 |
| | | 48h | — | — | 100 | 100 | 100 | 100 | 60 | — |
| 33 | SAW | | 0 | — | — | — | — | — | — | — |
| " | MBB | | 100 | 90 | 80 | 40 | 20 | — | — | — |
| " | BW | | 10 | — | — | — | — | — | — | — |
| " | TSM | | 50 | — | — | — | — | — | — | — |
| " | PA | | 80 | 85 | 30 | 0 | 0 | — | — | — |
| " | GPA | | 90 | 100 | 86 | 60 | 50 | — | — | — |
| " | SCR | 24h | — | — | — | 0 | 40 | 0 | 0 | 20 |
| | | 72h | — | — | — | 100 | 100 | 100 | 100 | 40 |

I claim:
1. A compound of the formula

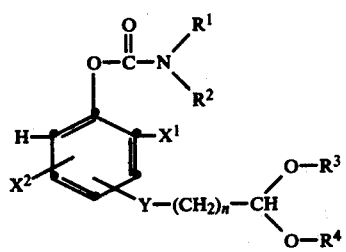

wherein $R^1$ is selected from the group consisting of hydrogen, alkyl and alkoxy; $R^2$ is selected from the group consisting of alkyl and alkenyl, $X^1$ and $X^2$ are each selected from the group consisting of hydrogen, alkyl and halogen; Y is selected from the group consisting of oxygen and sulfur; n is the integer 1 or 2; and $R^3$ and $R^4$ are each alkyl 2. The compound of claim 1, O-[4-(2,2-dimethoxyethoxy)phenyl]N-methylcarbamate.

3. The compound of claim 1, O-[3-(2,2-dimethoxyethoxy)-5-methylphenyl] N-methylcarbamate.

4. The compound of claim 1, O-[3-(2,2-dimethoxyethylthio)phenyl]N-methylcarbamate.

5. The compound of claim 1, O-[4-(3,3-dimethoxypropoxy)phenyl] N-allylcarbamate.